United States Patent [19]
Jones

[11] Patent Number: 5,218,143
[45] Date of Patent: Jun. 8, 1993

[54] PROCESS FOR PREPARING CARBOXYLIC ACIDS

[75] Inventor: Michael D. Jones, Hanworth, England

[73] Assignee: The British Petroleum Company p.l.c., London, England

[21] Appl. No.: 768,454

[22] Filed: Sep. 27, 1991

Related U.S. Application Data

[63] Continuation of Ser. No. 476,300, Feb. 7, 1990, abandoned.

[30] Foreign Application Priority Data

Feb. 23, 1989 [GB] United Kingdom ............... 8904125

[51] Int. Cl.$^5$ .................. C07C 51/10; C07C 51/12
[52] U.S. Cl. ................... 562/517; 562/519; 554/129; 554/132; 554/154
[58] Field of Search ............. 562/517, 519; 260/413; 554/129, 132, 154

[56] References Cited

U.S. PATENT DOCUMENTS

| | | | |
|---|---|---|---|
| 4,733,006 | 3/1988 | Singleton et al. | 562/517 |
| 4,894,477 | 1/1990 | Scates et al. | 562/519 |

Primary Examiner—José G. Dees
Assistant Examiner—Joseph M. Conrad, III
Attorney, Agent, or Firm—Brooks, Haidt, Haffner & Delahunty

[57] ABSTRACT

An improved liquid-phase process for preparing carboxylic acids having (n+1) carbon atoms by rhodium catalyzed carbonylation of an alcohol having n carbon atoms is provided. The process is particularly suitable for preparing acetic acid from methanol in commercial carbonylation reactors operating at steady-state with a low standing quantity of water (e.g. 0.5 to 5% by weight). The improvement lies in carrying out the carbonylation in the presence of an iodide stabilizer (e.g. lithium iodide) and a Group VI B metal costabiliser. The process can optionally be carried out in the presence of hydrogen.

8 Claims, No Drawings

PROCESS FOR PREPARING CARBOXYLIC ACIDS

This application is a continuation, of application Ser. No. 07/476,300, filed Feb. 7, 1990 now abandoned.

The present invention relates to a process for preparing a carboxylic acid having (n+1) carbon atoms (e.g. acetic acid where (n=1)) from an alcohol having n carbon atoms (e.g. methanol) by liquid phase carbonylation in the presence of a rhodium catalyst and an iodide promoter.

The preparation of acetic acid by the rhodium catalysed, iodide promoted carbonylation of methanol at elevated temperature and pressure is a well known process which is operated industrially. This particular reaction is an example of a genus of carbonylation reactions in which any alcohol having n carbon atoms can be transformed into a carboxylic acid having (n+1) carbon atoms by reaction with carbon monoxide. Such reactions are described further in for example GB 1233121 and Applied Industrial Catalysis, Vol 1 275-296 (1983). Acetic acid is itself a well known valuable commodity chemical.

On an industrial scale, the carbonylation of methanol to acetic acid is carried out under steady state conditions by continuously feeding methanol, carbon monoxide, catalyst, iodide promoter and recycled material to a carbonylation reactor whilst at the same time continuously withdrawing an acetic acid containing product stream. Under typical steady state conditions the carbonylation reaction is carried out in the presence of a standing quantity of 14-15% water to ensure good reaction rates (see EP 55618 and Ind. Eng. Chem. Prod. Res. Dev. 16 281-285 (1977)). The other main components in the reactor at steady state are acetic acid, methyl iodide and methyl acetate produced by the rapid esterification of methanol to acetic acid under the operating conditions.

It is known from EP 55618 and EP 161874 that a problem with such a process is that the rhodium catalyst tends to precipitate in those parts of the plant where the carbon monoxide overpressure is relatively low or in situations where the level of standing water in the reactor is less than the norm. This latter phenomenon causes a decrease in reactor productivity, if the process is operated with lower levels of water.

EP 161874 discloses that this problem can be overcome by the use of a catalyst stabiliser such as a soluble metal iodide or quaternary iodide salt. Especially suitable salts are the alkali metal iodides (e.g. lithium iodide) since these are the most soluble in the reaction medium. For low standing quantities of water, e.g. 1-4% by weight, 10-20% by weight of the iodide salt has been found particularly beneficial. It has also been found that productivities at low water levels are improved further if the reactor is operated under conditions such that, at steady state, the reactor contains 2-5% by weight methyl acetate. This is higher than conventionally used in industrially operated plants.

Whilst the suggestion described above provides a way of obtaining higher acetic acid productivity from a reactor operating with low standing water levels it is obviously desirable to increase productivity further if possible. This is particularly true since, even in the presence of a catalyst stabiliser, the productivity is still dependent to a certain extent upon the level of water. Thus, in view of the above, the problem to be solved is to improve acetic acid productivity from a reactor operating at low water levels with a catalyst stabiliser.

One solution to this problem, described in EP 0250189, is to add at least 4 psig of hydrogen gas to the carbonylation reactor. Another solution which has now been discovered is to add effective amounts of a Group VIB metal costabiliser.

According to the present invention there is provided a liquid-phase process for preparing a carboxylic acid having (n+1) carbon atoms by reaction of carbon monoxide with an alcohol having n carbon atoms in the presence of a rhodium catalyst at elevated temperature and pressure which process comprises feeding the alcohol and/or an ester of the alcohol and the carboxylic acid together with carbon monoxide to a carbonylation reactor and removing the carboxylic acid from the carbonylation reactor characterised in that the carbonylation reactor contains during the course of the process a liquid reaction medium comprising:

(a) at least a finite quantity of water,
(b) a catalyst stabiliser selected from iodide salts which are soluble in the reaction medium at the temperature of the reaction,
(c) a Group VIB metal costabiliser,
(d) the iodide derivative of the alcohol,
(e) the ester of the carboxylic acid and the alcohol,
(f) a rhodium catalyst, and
(g) the carboxylic acid.

The invention solves the problem defined above by employing a Group VIB metal costabiliser to enhance the rate of acetic acid production. Whilst not wishing to be bound by any theory, preliminary evidence from infrared spectroscopy suggests that the presence of the Group VIB metal costabiliser increases the concentration of catalytically active rhodium species $Rh(CO)_2I_2^-$ in the carbonylation reactor relative to other less reactive or inactive forms.

The process which comprises the present invention can be applied to the conversion of any alcohol having n carbon atoms into any carboxylic acid having (n+1) carbon atoms. The process is especially suitable, however, when an alcohol having from one to six carbon atoms is to be carbonylated. Preferably, the process is employed to convert either methanol to acetic acid or ethanol to propionic acid with the former of these being the most preferred. Whilst, for the rest of the description, the invention will be discussed in terms of the methanol to acetic acid process, it will be appreciated that all statements are applicable to other alcohol feedstocks with the appropriate obvious modifications.

As regards the rhodium catalyst, it is now well known that initially any rhodium source, including the metal itself, salts, complexes etc, can be introduced into the carbonylation reactor. This is because, under the reaction conditions, all such sources are converted into a common catalytically active species. It is believed that this species is the anion $Rh(CO)_2I_2^-$.

Whilst the process can be operated at a carbon monoxide partial pressures as low as 1 atmosphere, a preferred range of partial pressures for industrial operation is from 2 to 100, most preferably 5 to 20 atmospheres. The process is preferably carried out at a temperature in the range 70° to 220° C., most preferably 140° to 190° C.

The process of the present invention is suitably operated by (a) continuously feeding methanol, methyl acetate or mixtures thereof to a carbonylation reactor together with recycle streams, carbon monoxide and optionally hydrogen and (b) continuously withdrawing an acetic acid containing product stream. During such continuous operation the reactor is maintained at a steady state composition in which the primary components in the liquid phase are methyl acetate, methyl iodide, hydrogen iodide, acetic acid, water, rhodium, catalyst stabiliser and Group VIB metal costabiliser. Secondary components, e.g. side products etc may also be present in small amounts. Preferably the steady state composition of the liquid phase is such that the primary components, excluding acetic acid, which together with impurities and the secondary components constitute the balance of the liquid phase, fall within the following broad and preferred ranges:

|  | Broad Wt % | Preferred Wt % |
| --- | --- | --- |
| Water | 0.1-15 | 0.5-5 |
| Methyl Acetate | 0.1-6 | 1-6 |
| Methyl Iodide | 5-20 | 10-16 |
| Rhodium (ppm) | 100-1000 | 250-750 |
| Catalyst Stabiliser (as LiI) | 2-20 | 10-20 |
| Group VIB Costabiliser (as Mo(CO)$_6$) (ppm) | 0-10,000 | 1-5000 |

The catalyst stabiliser, as is indicated in EP 161874, can be any metal iodide or quaternary ammonium iodide salt. Preferred examples of the metal iodide salts are the alkali and alkaline earth metals including lithium iodide, sodium iodide, potassium iodide, caesium iodide, magnesium iodide and calcium iodide. Such iodide salts are preferred because they have reasonable solubility in the reaction medium. It is believed that in the case of the alkali and alkaline earth metal iodides the nature of the cation is relatively unimportant and that it is the presence of solubilised iodide ion in the reaction medium that causes the improvement. That being the case, the most preferred metal iodide is lithium iodide which has the greatest solubility in the reaction medium.

The metal iodide salt can be introduced directly into the carbonylation reactor. Alternatively the iodide salt can be generated in situ since under the operating conditions of the carbonylation reactor a wide range of metal salts will react with methyl iodide to general the metal iodide. Preferred metal salts which can be used in this way are the $C_1$ to $C_6$ carboxylate salts e.g. the acetate or propionate salts.

Soluble quaternary ammonium or phosphonium iodides can be used as alternatives to the metal iodides. These iodides can also be either added directly or generated in situ. Typical quaternary ammonium iodides are those where the cation has been obtained by quaternisation of a tertiary amine, pyridine, pyrollidine, imidazole or other heterocyclic nitrogen containing compound.

The Group VIB metal costabilisers can be any of the metals designated as being in Group VIB of the Periodic Table as defined in Cotton and Wilkinson "Advanced Inorganic Chemistry", 3rd Edition, i.e. chromium, molybdenum and tungsten most preferably molybdenum and tungsten. Whilst these metals can be added to the reaction medium in any form, it is preferred to use a low valent salt, such as molybdenum, chromium or tungsten acetate or iodide, or a carbonyl complex such as $Mo(CO)_6$, $W(CO)_6$, $Cr(CO_6)$ and the like.

The behaviour of the Group VIB metals in further increasing acetic acid productivity is surprising and not a phenomenon apparently shared by all other transition metals. A case in point is iron, the effect of which is to actually reduce reactor productivity. This discovery is particularly important because on an industrial plant corrosion leads to a build up of iron, molybdenum, tungsten, chromium and nickel salts in the reactor. It would appear that this build up of such metal salts has previously been viewed as detrimental, presumably because of the presence of the iron. Thus, previously, methods have been developed to remove all corrosion metals from the reaction medium (e.g. U.S. Pat. No. 4,628,041 and EP 265146). It is now however apparent that there is no need to remove chromium, molybdenum and tungsten from the reaction medium.

Hence, in an embodiment of the present invention, there is provided a process for treating process streams, arising in the manufacture of acetic acid from methanol, which process streams contain rhodium and typical corrosion metal salts characterised in that the process comprises selectively removing all the corrosion metals from the process stream with the exception of chromium, molybdenum or tungsten salts.

Selective removal of for example iron from a process stream containing rhodium, iron, chromium, molybdenum and tungsten can be achieved by the use of selective ion exchange resins, electrodialysis, selective precipitation and the like. The process defined by the embodiment is of course also applicable to process streams which arise during the carbonylation of any n carbon atom alcohol to (n+1) carbon atom carboxylic acid.

The invention is now illustrated by the following Examples.

EXAMPLE 1

Use of Molybdenum Carbonyl as Costabiliser

A 150 ml Hastelloy autoclave was charged with AcOH (32.2 g), MeOAc (17.7 g), $H_2O$ (2.95 g), MeI (28.1 g), LiOAc.2H$_2$O (8.609 g), and a solution containing $Mo(CO)_6$ (0.82 g), aq.HI (57% solution, 1.45 g) and AcOH (4.0 g). The autoclave was sealed, purged with $N_2$ (3×40 barg), pressurised with $N_2$ (3 barg) and heated to 185° C. and allowed to stabilise for 25 minutes. To the autoclave was injected 35 [RhCl(CO)$_2$]$_2$ (0.06 g) in AcOH (5.84 g) under a pressure of CO. The CO was continually fed via a pressure regulating valve such that the autoclave pressure remained constant at about 36 barg. CO was fed from a ballast vessel and the pressure was measured using a transducer reading to 0.1 bar. The gas uptake rate at a position corresponding to a solution composition of MeOAc 5% w/w and $H_2O$ (2% w/w) was measured as 7.6 mol/1 h).

Comparative Experiment A-No Group VI B Metal Present

A 150 ml Hastelloy autoclave was charged with AcOH (38.2 g), MeOAc (17.76 g), $H_2O$ (3.56 g), MeI (27.9 g) and LiOAc.2H$_2$O (8.60 g). The autoclave was sealed, purged and heated to 185° C. as described in Example 1. The catalyst solution [RhCl(CO)$_2$]$_2$ (0.06 g) in AcOH (5.48 g) was injected into the autoclave using an overpressure of CO which was again fed to the autoclave on demand via a back pressure regulator from a reservoir vessel. The gas uptake rate at a position corresponding to a solution composition of MeOAc (5% w/w) and $H_2O$ (2% w/w) was measured as 5.9 mol/1 h.

Comparative Experiment B-Effect of Iron

A 150 ml Hastelloy autoclave was charged with AcOH (32.2 g), MeOAc (17.7 g), $H_2O$ (2.2 g), MeI (27.9 g), LiOAc.2H$_2$O (8.6 g) and a solution containing basic iron acetate (1.3 g), aqueous HI (57% solution 3.2 g) and AcOH (3.0 g). The autoclave was sealed, purged and heated to 185° C. as described in Example 1. The catalyst solution [RhCl(CO)$_2$]$_2$ (0.06 g) in AcOH (5.85 g) was injected into the autoclave using an overpressure of CO. The gas uptake rate at a postition corresponding to a solution composition of MeOAc (5% w/w) and H$_2$O (2% w/w) was measured as 1.9 mol/1 h. This Example shows that not all corrosion metals have a beneficial effect on reaction rate.

EXAMPLE 2

Use of Chromium Acetate as Costabiliser

A 150 ml Hastelloy autoclave was charged with AcOH (32.2 g), MeOAc (17.66 g), H$_2$O (3.1 g), MeI (27.9 g), LiOAc.2H$_2$O (8.6 g) and a solution of chromium acetate (1.51 g), aqueous HI (57% solution, 1.1 g) and AcOH (4.0 g). The autoclave was sealed, purged and heated to 185° C. as described in Example 1. The catalyst solution [RhCl(CO)$_2$]$_2$ (0.06 g) in AcOH (5.84 g) was injected into the autoclave using an overpressure of CO. The gas uptake rate at the position corresponding to a solution composition of MeOAc (5% w/w) and H$_2$O (2% w/w) was measured as 6.5 mol/1 h.

EXAMPLE 3

Use of Tungsten Carbonyl as Costabiliser

The autoclave was charged with AcOH (32.2 g), MeOAc (17.7 g), H$_2$O (2.85 g), MeI (27.9 g), LiOAc.2H$_2$O (8.6 g) and a solution of [W(CO)$_6$] (1.1 g), aqueous HI (57% solution, 1.4 g) and AcOH (4.0 g). The autoclave was sealed, purged and heated to 185° C. as described in Example 1. The catalyst solution [RhCl(CO$_2$]$_2$ (0.061 g), in AcOH (5.84 g) was injected into the autoclave using an overpressure of CO. The gas uptake rate at the position corresponding to a solution composition of MeOAc (5% w/w) and H$_2$O (2% w/w) was measured as 9.2 mol/1 h.

EXAMPLE 4

Use of Chromium Carbonyl as Costabiliser

The autoclave was charged with AcOH (32.2 g), MeOAc (17.7 g), H$_2$O (2.85 g), MeI (27.9 g), LiOAc.2H$_2$O (8.6 g) and a solution of [Cr(CO)$_6$] (0.55 g), aqueous HI (57% solution, 1.1 g) and AcOH (4.0 g). The autoclave was sealed, purged and heated to 185° C. as described in Example 1. The catalyst solution [RhCl(CO$_2$]$_2$ (0.061 g), in AcOH (5.84 g) was injected into the autoclave using an overpressure of CO. The gas uptake rate at the position corresponding to a solution composition of MeOAc (5% w/w) and H$_2$O (2% w/w) was measured as 7.1 mol/1 h.

EXAMPLE 5

Use of Molybdenum Carbonyl as Costabiliser

A solution of [Mo(CO)$_6$] in AcOH (31.5 g) was heated for 24 hours at 80° C. in a sealed Schlenck tube. The resultant solution was cooled and transferred to an autoclave containing AcOH (4.8 g), MeOAc (17.6 g), H$_2$O (2.9 g), MeI (27.9 g), LiOAc.2H$_2$O (8.61 g). The autoclave was sealed, purged and heated to 185° C. as described in Example 1. The catalyst solution [RhCl(CO$_2$]$_2$ (0.061 g), in AcOH (5.84 g) was injected into the autoclave using an overpressure of CO. The gas uptake rate at the position corresponding to a solution composition of MeOAc (5% w/w) and H$_2$O (2% w/w) was measured as 8.1 mol/1 h.

EXAMPLE 6

Use of Molybdenum Carbonyl as Costabiliser

A 150 ml Hastelloy autoclave was charged with AcOH (32.2 g), MeOAc (17.6 g), H$_2$O (3.5 g), MeI (28.5 g), LiOAc.2H$_2$O (8.6 g) and [Mo(CO)$_6$] (0.82 g). The autoclave was sealed, purged and heated to 185° C. as described in Example 1. The catalyst solution [RhCl(CO)$_2$]$_2$ (0.06 g) in AcOH (5.84 g) was injected into the autoclave using an overpressure of CO. The gas uptake rate at the position corresponding to a solution composition of MeOAc (5% w/w) and H$_2$O (2% w/w) was measured as 8.5 mol/1 h.

EXAMPLE 7

Use of Molybdenum Carbonyl as Costabiliser

A 150 ml Hastelloy autoclave was charged with AcOH (36.2 g), MeOAc (17.65 g), H$_2$O (3.55 g), MeI (29.1 g), LiOAc.2H$_2$O (8.6 g) and [Mo(CO)$_6$] (1.64 g). The autoclave was sealed, purged and heated to 185° C. as described in Example 1. The catalyst solution [RhCl(CO)$_2$]$_2$ (0.06 g) in AcOH (5.84 g) was injected into the autoclave using an overpressure of CO. The gas uptake rate at the position corresponding to a solution composition of MeOAc (5% w/w) and H$_2$O (2% w/w) was measured as 7.9 mol/1 h.

EXAMPLE 8

Use of Molybdenum Carbonyl as Costabiliser

The autoclave was charged with AcOH (36.2 g), MeOAc (17.65 g), H$_2$O (3.5 g), MeI (27.88 g), LiOAc.2H$_2$O (8.6 g) and [Mo(CO)$_6$] (0.41 g). The autoclave was sealed, purged and heated to 185° C. as described in Example 1. The catalyst solution [RhCl(CO$_2$]$_2$ (0.06 g), in AcOH (5.84 g) was injected into the autoclave using an overpressure of CO. The gas uptake rate at the position corresponding to a solution composition of MeOAc (5% w/w) and H$_2$O (2% w/w) was measured as 7.1 mol/1 h.

EXAMPLE 9

Use of Molybdenum Carbonyl as Costabiliser

The autoclave was charged with AcOH (36.2 g), MeOAc (17.68 g), H$_2$O (3.53 g), MeI (28.0 g), LiOAc.2H$_2$O (8.6 g) and a [Mo(CO)$_6$] (0.14 g). The autoclave was sealed, purged and heated to 185° C. as described in Example 1. The catalyst solution [RhCl(CO$_2$]$_2$ (0.06 g), in AcOH (5.84 g) was injected into the autoclave using an overpressure of CO. The gas uptake rate at the position corresponding to a solution composition of MeOAc (5% w/w) and H$_2$O (2% w/w) was measured as 6.6 mol/1 h.

EXAMPLE 10

Use of Molybdenum Acetate as Costabiliser

The autoclave was charged with AcOH (32.2 g), MeOAc (17.64 g), H$_2$O (2.95 g), MeI (28.0 g), LiOAc.2H$_2$O (8.606 g), and a solution of molybdenum acetate (0.67 g), a.q. HI (57% solution 1.41 g) and AcOH (4.0 g). The autoclave was sealed, purged with N$_2$ and heated to 185° C. as in Example 1. The catalyst solution [RhCl(CO)$_2$]$_2$ (0.06 g) in AcOH (5.84 g) was injected into the autoclave using an overpressure of CO. The gas uptake rate at the position corresponding to a solution composition of MeOAc (5% w/w) and H₂O (2% w/w) was measured as 7.6 mol/l h.

Comparative Test-Use of Vanadium Acetoacetonate

The autoclave was charged with AcOH (36.2 g), MeOAc (17.66 g), H₂O (3.55 g), MeI (28.0 g), LiOAc.2-H₂O (8.60 g), and V(acac)₂ (1.1 g). The autoclave was sealed, heated to 185° C. as in Example 1. The catalyst solution [RHCl(CO)₂]₂ (0.061 g) in AcOH (5.84 g) was injected into the autoclave using an overpressure of CO. The gas uptake rate measured at a solution composition of MeOAc (5% w/w) and H₂O (2% w/w) was measured as 5.9 mol/l h.

I claim:

1. A liquid-phase process for preparing a carboxylic acid having (n+1) carbon atoms by reaction of carbon monoxide with an alcohol having n carbon atoms in the presence of a rhodium catalyst at elevated temperature and pressure which process comprises feeding the alcohol and/or an ester of the alcohol and the carboxylic acid together with carbon monoxide to a carbonylation reactor and removing the carboxylic acid from the carbonylation reactor characterised in that the carbonylation reactor contains during the course of the process a liquid reaction medium comprising:
   (a) at least a finite quantity of water,
   (b) a catalyst stabiliser selected from iodide salts which are soluble in the reaction medium at the temperature of the reaction,
   (c) a metal costabiliser consisting essentially of one or more Group VI B metals,
   (d) the iodide derivative of the alcohol,
   (e) the ester of the carboxylic acid and the alcohol,
   (f) a rhodium catalyst, and
   (g) the carboxylic acid.

2. A liquid-phase process as claimed in claim 1 characterised in that the carboxylic acid is acetic acid and the alcohol is methanol.

3. A liquid-phase process as claimed in claim 2 characterised in that the level of water is 0.5 to 5% of the total weight of the reactor contents.

4. A liquid-phase process as claimed in claim 3 characterised in that the level of methyl acetate in the reactor is 1 to 6% of the total weight of the reactor contents.

5. A liquid-phase process as claimed in claim 4 characterised in that the catalyst stabiliser is an alkali metal iodide.

6. A liquid-phase process as claimed in claim 5 characterised in that the Group IV B metal costabiliser is either a molybdenum or tungsten costabliser.

7. A liquid-phase process as claimed in claim 6 characterised in that the Group IV B metal costabiliser is a low valent molybdenum or tungsten salt or a molybdenum or tungsten carbonyl.

8. A liquid-phase process as claimed in claim 1 wherein the Group VI B metal costabilizer is deliberately added to the reaction medium.

* * * * *

UNITED STATES PATENT AND TRADEMARK OFFICE
CERTIFICATE OF CORRECTION

PATENT NO. : 5,218,143
DATED : June 8, 1993
INVENTOR(S) : MICHAEL D. JONES

It is certified that error appears in the above-indentified patent and that said Letters Patent is hereby corrected as shown below:

Cover Page, last line, should read, "7 claims, No Drawings"

Claim 1, col. 8, line 6, should read "(g) the carboxylic acid, wherein said co-stabilizer(s) is deliberately added.

Claim 8 should be cancelled.

Signed and Sealed this

First Day of March, 1994

Attest:

BRUCE LEHMAN

Attesting Officer        Commissioner of Patents and Trademarks